US006884393B2

(12) United States Patent
Hui et al.

(10) Patent No.: US 6,884,393 B2
(45) Date of Patent: Apr. 26, 2005

(54) SURFACE TREATMENT OF ALUMINUM ALLOYS TO IMPROVE STERILIZATION PROCESS COMPATIBILITY

(75) Inventors: Henry K. Hui, Laguna Niguel, CA (US); Les A. Feldman, Calabasas Hills, CA (US); Nancy Chu, Laguna Niguel, CA (US); Su-Syin Wu, Irvine, CA (US)

(73) Assignee: Ethicon, Inc., Somerville, NJ (US)

( * ) Notice: Subject to any disclaimer, the term of this patent is extended or adjusted under 35 U.S.C. 154(b) by 499 days.

(21) Appl. No.: 09/904,667

(22) Filed: Jul. 13, 2001

(65) Prior Publication Data

US 2003/0053930 A1 Mar. 20, 2003

(51) Int. Cl.$^7$ .............. A61L 9/00; B01J 19/00; C25D 3/30; B65D 83/10; A61B 17/06
(52) U.S. Cl. ............... 422/28; 422/1; 422/4; 422/7; 422/40; 422/305; 422/306; 205/300; 206/72; 206/363; 206/364; 206/365; 206/438; 206/563
(58) Field of Search .............. 422/1, 4, 7–9, 422/28, 40, 305–306; 205/300; 206/72, 363–365, 438, 563

(56) References Cited

U.S. PATENT DOCUMENTS

| | | | | |
|---|---|---|---|---|
| 3,634,937 A | * | 1/1972 | Green ................. 434/263 |
| 3,937,571 A | | 2/1976 | Krulik et al. ........... 355/3 R |
| 3,940,270 A | | 2/1976 | Krulik et al. ........... 96/1.4 |
| 3,961,111 A | | 6/1976 | Smith, deceased ........ 427/419 |
| 4,023,899 A | | 5/1977 | Hayashi et al. ......... 355/10 |
| 4,117,085 A | * | 9/1978 | Yang et al. ............ 423/264 |
| 4,180,443 A | | 12/1979 | Darrow ................. 204/35 N |
| 4,201,821 A | | 5/1980 | Fromson et al. ......... 428/203 |
| 4,230,492 A | | 10/1980 | Thomas ................. 430/159 |
| 4,256,547 A | | 3/1981 | Turns et al. ........... 204/35 N |
| 4,288,299 A | | 9/1981 | Carter ................. 204/35 N |
| 4,310,390 A | | 1/1982 | Bradley et al. ........ 204/37 R |
| 4,413,049 A | | 11/1983 | Beaudet et al. ......... 430/126 |
| 4,431,707 A | | 2/1984 | Burns et al. ........... 428/629 |
| 4,489,002 A | | 12/1984 | Baumann et al. ........ 534/695 |
| 4,525,247 A | | 6/1985 | McMonagle ............. 204/24 |
| 4,532,065 A | | 7/1985 | Cohen et al. ........... 252/135 |
| 4,580,713 A | | 4/1986 | Sekibata et al. ......... 228/111 |
| 4,617,178 A | * | 10/1986 | Nichols ................. 422/310 |
| 4,633,035 A | | 12/1986 | McMonagle ............. 174/68.5 |
| 4,681,655 A | | 7/1987 | Potter ................. 156/632 |
| 4,731,317 A | | 3/1988 | Fromson et al. ......... 430/159 |
| 4,795,777 A | | 1/1989 | Higginbotham et al. .... 524/441 |
| 4,925,738 A | | 5/1990 | Tsuya et al. ........... 428/472.2 |
| 4,958,511 A | | 9/1990 | Marcus ................. 73/7 |
| 5,064,083 A | * | 11/1991 | Alexander et al. ....... 215/247 |
| 5,091,287 A | | 2/1992 | Dustin ................. 430/302 |
| 5,166,020 A | | 11/1992 | Fukuda et al. .......... 430/58 |
| 5,354,286 A | * | 10/1994 | Mesa et al. ........... 604/230 |
| 5,658,529 A | * | 8/1997 | Feldman et al. ......... 422/23 |
| 5,705,225 A | | 1/1998 | Dornfest et al. ........ 427/248 |
| 6,027,851 A | | 2/2000 | Coppens et al. ......... 430/204 |

OTHER PUBLICATIONS

"Anodic Coatings for Aluminum and Aluminum Alloys", Anodic, Inc., MIL–A8625F, (Sep. 10, 1993).
"Anodic Coatings for Aluminum and Aluminum Alloys", Anodic, Inc., MIL–A8625E, (Apr. 25, 1988).
"CGX Series, Operating and Service Instructions", CMI–Coating Measurement Instruments, pp. 1–25, (1998).
Wernick, S., et al., "The Surface Treatment and Finishing of Aluminum and its Alloys", Finishing Publications, Ltd., 5$^{th}$ Edition, vol. 1, pp. 288–295 (1987).
Wernick, S., et al., "The Surface Treatment and Finishing of Aluminum and its Alloys", Finishing Publications, Ltd., 5$^{th}$ Edition, vol. 2, pp. 860–865 (1987).

* cited by examiner

*Primary Examiner*—Robert J. Warden, Sr.
*Assistant Examiner*—Monzer R. Chorbaji

(57) ABSTRACT

Disclosed herein are methods of sterilizing a device in a sterilizer, methods of sterilizing a device in an enclosure in a sterilizer, and enclosures for retaining a device capable of being sterilized in a sterilization process. The sterilization process comprises hydrogen peroxide vapor or gas. The sterilization load may include an enclosure, which can be a tray or a container. The tray or container comprises at least a volume of aluminum oxide. The ratio of the amount of hydrogen peroxide gas or vapor introduced into the sterilizer to the volume of aluminum oxide is at least 24 mg/cm$^3$.

24 Claims, No Drawings

SURFACE TREATMENT OF ALUMINUM ALLOYS TO IMPROVE STERILIZATION PROCESS COMPATIBILITY

BACKGROUND OF THE INVENTION

Aluminum alloys are used for a number of resterilizable medical device applications, such as sterilization containers and trays, which can have large amounts of surface area. Containers and trays are used to retain the devices to be sterilized. Normally, a sterilization load comprises all the devices to be sterilized that are placed in packaging, which could be a container, tray, wrapping barrier, and/or pouch. Sterilization containers are designed to allow sterilization of medical devices and can be used to store the medical devices after sterilization and prior to use for a predetermined period. Containers typically comprise at least one filter that acts as a microbial barrier but allows sterilizing gas or vapor to diffuse into and out of the container. The instruments in the container can therefore remain sterile during storage because the container functions as a microbial barrier, preventing the instruments from becoming re-contaminated and nonsterile. On the other hand, an instrument sterilization tray normally does not comprise a gas or vapor permeable microbial impermeable barrier. The tray itself cannot maintain the sterility of the instrument in the tray after the sterilization process. It requires gas or vapor permeable and microorganism impermeable wrapping barrier outside of the tray to allow the diffusion of sterilizing agent into and out of the wrapped tray, to prevent the penetration of microorganisms into the wrapped tray, and to maintain the sterility of devices in the wrapped tray after sterilization. The tray may have a lid and the lid does not constitute a sterile barrier. Depending on the need and application, various dimensions of container and tray can be manufactured. An advantage of sterilization containers over trays for some users is that they eliminate the large amounts of disposable sterilization wrap used when sterilizing instruments in trays. This reduces disposal costs and environmental concerns.

Sterilization containers or trays commonly are made from anodized aluminum. Aluminum is used because of its light weight, good thermal conductivity, and corrosion resistance properties. Aluminum is usually anodized to improve its durability as well as resistance to corrosion (such as described in Mil Standard MIL-A-8625F for anodized aluminum, US Department of Defense, Military Specification MIL-A-8625F, pp. 1–19, Sep. 10, 1993). Standard anodized aluminum surface finishes contain very fine internal porosity, and a sterilizing agent such as hydrogen peroxide vapor can be absorbed into the porous layer. For a sterilization load with a large surface area, the absorption of sterilizing agent such as hydrogen peroxide may interfere with sterilization efficacy by reducing the amount of hydrogen peroxide available in the vapor phase in the chamber. This can be due to a combination of 1) large amounts of surface area of the device in combination with the large effective surface area of the anodization layer, and 2) penetration or diffusion of the hydrogen peroxide vapor past the outer liquid-repellent coating on the anodized surface to become absorbed by the inner porous oxide layer.

In the typical aluminum anodization process, such as a Type II process (U.S. Pat. No. 5,658,529 and U.S. Military Specification Mil-A-8625E, "Anodic Coatings for Aluminum and Aluminum Alloys," Apr. 25, 1988, both of which are incorporated herein by reference in their entirety) aluminum is anodized in an aqueous solution of 95 mL/L $H_2SO_4$ for 30 minutes with a direct current of 15 to 21 volts and at a density of 9 to 12 A/sq. ft. Following the anodizing step, the aluminum oxide layer is sealed in boiling water or an aqueous solution of nickel acetate (5–5.8 g/L) for 30 minutes. The sealing process causes hydration of the aluminum oxide layer, which makes it impermeable to liquid.

Anodized aluminum coatings are inherently porous. This is due to the fact that the coating is produced electrolytically by anodic oxidation of aluminum. As the oxidized layer becomes thicker, there are two basic competing processes that occur (Wernick, et al, "The Surface Treatment and Finishing of Aluminum and its Alloys," Vol. 1, $5^{th}$ Ed., ASM International, Metals Park, Ohio, Chap. 6, p. 290). At the same time as the oxide coating is forming, it is being redissolved by the electrolyte. As the oxide layer builds up, it tends to limit the electrolytic current flow, because the oxide layer is relatively non-conducting. However, due to the re-dissolution of the oxide, pores begin to form in the oxide layer. These pores produce channels of high conductivity by locally thinning the oxide layer, allowing the liquid electrolyte to penetrate close to the metal substrate, while oxide and hydroxide crystals build up on the surface of the film, increasing the overall thickness. As long as the pores remain accessible to the electrolyte, the current can continue to flow and the film will grow further. The solubility of the oxides and hydroxides in the electrolyte can affect the porosity. Borate and tartrate electrolytes, with a low solubility for the oxides, tend to produce thin, dense coatings with low porosity. The coatings stop growing at relatively low thickness due to the high resistance of the less porous oxide layer. Sulfuric acid electrolytes tend to allow for faster dissolution of the oxide, allowing the pores to form and providing practical film thickness of 0.1 to 1.2 mm.

The most reliable non-destructive method for measuring film thickness uses eddy-current measurements (Wernick, et al., Chap. 12, p. 864). The eddy-current method, which is practical, non-destructive, fast and economical, is commonly used in commercial anodization facilities to verify film thickness and as a QC measurement technique. Research methods to measure film porosity have included lead acetate absorption, oil absorption, gas absorption (BET method), toluene absorption, electrolytic pore filling, reflectance methods, dielectric constant measurements, electron microscopy, and permeability (Wernick, et al, Chap. 12, pp. 878–882). However, porosity measurements, which tend to be time consuming and expensive, are not commonly used commercially as a process control or QC method.

SUMMARY OF THE INVENTION

Disclosed herein is a method of sterilizing a device in a sterilizer, comprising placing the device into the sterilizer, where the sterilizer contains a sterilization load and the sterilization load comprises an enclosure, the enclosure comprises at least one aluminum surface and the at least one aluminum surface comprises a volume of aluminum oxide; introducing an amount of hydrogen peroxide gas or vapor into the sterilizer, where the ratio of the amount of hydrogen peroxide gas or vapor introduced into the sterilizer to the volume of aluminum oxide is at least 24 $mg/cm^3$; and sterilizing the device in the sterilizer.

Also disclosed is an enclosure for retaining a device capable of being sterilized in a sterilization process, the sterilization process comprising hydrogen peroxide, the enclosure comprising a plurality of walls and a bottom surface defining an interior space, the interior space capable of retaining the device; at least one aluminum surface exposed to the interior, the at least one aluminum surface comprising a volume of aluminum oxide; and a material coated on the at least one aluminum surface, where the material is substantially impermeable to hydrogen peroxide gas or vapor. The enclosure can be a tray or a container.

Additionally disclosed is a method of sterilizing a device in an enclosure, comprising placing the device in said enclosure, where the enclosure comprises at least one aluminum surface, where the at least one aluminum surface comprises a volume of aluminum oxide and a material coated on the aluminum oxide; the material being substantially impermeable to hydrogen peroxide gas or vapor; placing the enclosure into the sterilizer; introducing an amount of hydrogen peroxide gas or vapor into the sterilizer; and sterilizing the device in the sterilizer. The enclosure can be a tray or a container.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

DETAILED DESCRIPTION OF THE PREFERRED EMBODIMENT

Certain aspects of the present invention are directed towards sterilizing medical devices. Medical devices that come into contact with the body of a patient may contain microorganisms that can cause disease or infection in the body of the patient. Therefore, it is desirable to sterilize these devices prior to their contact with the body of the patient, or prior to their presence in the same environment, such as an operating room, as the patient.

Although some aspects of the invention are at times disclosed in terms of medical devices, it is understood that the methods of the present invention may be practiced to sterilize any device, object, or instrument, whether comprising aluminum or not.

A method of sterilizing a device is to expose the device to hydrogen peroxide gas or vapor. Certain aluminum surfaces, such as those comprising a container or a tray holding the device to be sterilized, or an aluminum surface on the device itself, are somewhat permeable to hydrogen peroxide. Hydrogen peroxide molecules can enter the surface of the aluminum surface and reside there. As a result, not enough hydrogen peroxide would be available in the atmosphere to sterilize the device.

Thus, in one aspect, the present invention relates to a method of sterilizing a device in a sterilizer, comprising placing the device into the sterilizer, where the sterilizer contains a sterilization load and the sterilization load comprises an enclosure, the enclosure comprises at least one aluminum surface and the at least one aluminum surface comprises a volume of aluminum oxide; introducing an amount of hydrogen peroxide gas or vapor into the sterilizer, where the ratio of the amount of hydrogen peroxide gas or vapor introduced into the sterilizer to the volume of aluminum oxide is at least 24 $mg/cm^3$; and sterilizing the device in the sterilizer.

In certain embodiments, the aluminum in the above method is anodized aluminum, while in other embodiments the aluminum is raw aluminum.

The aluminum surface in the above method may be coated with a material. The material may be a polymer. In certain embodiments, the material may be permeable to hydrogen peroxide gas or vapor.

In some embodiments, the device to be sterilized is put in an aluminum sterilization enclosure, which may be a container, and the enclosure is placed into the sterilizer. The enclosure preferably comprises at least one barrier, which may be permeable to gas or vapor and impermeable to microorganisms. In certain embodiments, the ratio of the amount of hydrogen peroxide gas or vapor introduced into the sterilizer to the volume of aluminum oxide is at least 47 $mg/cm^3$. In other embodiments of the invention, the enclosure is a tray.

Some embodiments include a barrier that is impermeable to microorganisms, such that the barrier does not allow any microorganisms to pass through. In other embodiments, the impermeable barrier may allow some microorganisms to pass through; however, the level of microorganisms on the sterilized side of the barrier will remain low enough such that, given the standards of sterility, the sterilized side of the barrier will be considered by those of skill in the art to remain sterilized. The standards of sterility are known to those of skill in the art and may vary from one application to another.

In another aspect, the present invention relates to an enclosure for retaining a device capable of being sterilized in a sterilization process, the sterilization process comprising hydrogen peroxide, the enclosure comprising a plurality of walls and a bottom surface defining an interior space, and the interior space capable of retaining the device. At least one aluminum surface is exposed to the interior, the aluminum surface comprising a volume of aluminum oxide. The device is coated with a material, where the material is substantially impermeable to hydrogen peroxide gas or vapor. The enclosure can be a tray or a container.

In some embodiments, the material that is impermeable to hydrogen peroxide gas or vapor is a material that does not allow hydrogen peroxide gas or vapor to pass through it. In other embodiments, the impermeable material may allow small amounts of hydrogen peroxide gas or vapor to pass through it; however, the amount of hydrogen peroxide gas or vapor permeated through the impermeable barrier is less than 10%, or less than 5%, or less than 2%, or less than 1% of the amount of hydrogen peroxide gas or vapor introduced.

In certain embodiments, the aluminum in the above method is anodized aluminum, while in other embodiments the aluminum is raw aluminum.

In some embodiments, the material coating the aluminum surface is a polymer, which may be a polyaromatic polymer. A "polyaromatic polymer" is a polymer that is made from a monomer that contains at least one aromatic substituent. In certain embodiments, the polymer is Parylene. In some embodiments, the Parylene coating thickness is at least 0.0001 mm. More preferably, the Parylene coating thickness is at least 0.0004 mm. Most preferably, the Parylene coating thickness is at least 0.025 mm. "Parylene" is a polymer well-known to those of skill in the art. It can be made by polymerizing di-para-xylylene using methods well-known in the art.

In another aspect, the invention relates to a method of sterilizing a device in an enclosure. The method comprises placing the device in the enclosure, where the enclosure comprises at least one aluminum surface, and the aluminum surface comprises a volume of aluminum oxide and a material coated on the aluminum oxide; the material is substantially impermeable to hydrogen peroxide gas or vapor. The enclosure is placed into the sterilizer; an amount of hydrogen peroxide gas or vapor is introduced into the sterilizer; and the device in the sterilizer is sterilized. The enclosure can be a tray or a container.

In certain embodiments, the aluminum in the above method is anodized aluminum, while in other embodiments the aluminum is raw aluminum.

In some embodiments, the material coating the aluminum surface is a polymer, which may be a polyaromatic polymer. In certain embodiments, the polymer is Parylene.

The enclosure previously referred may be a container with at lease one gas or vapor permeable microorganism impermeable barrier, a tray, or a sheet. The container comprises a plurality of walls, a bottom surface and a lid for placing and removing the devices into and out of the container. The tray comprises a plurality of walls and a bottom surface. Optionally, the tray may have a lid for stacking purposes. The sheet comprises a flat plate. Both tray and sheet require additional gas or vapor permeable microorganism impermeable wrapping barrier to protect the devices from contamination by the microorganisms located outside of the wrapped tray or sheet.

While the described embodiments represent certain preferred embodiments of the present invention, it is to be understood that modifications will occur to those skilled in the art without departing from the spirit of the invention. The scope of the invention is therefore to be determined solely by the appended claims.

The present invention describes methods of surface finishing for aluminum that provide good efficacy, durability, corrosion resistance, long life, and also maintain the sterility of the devices. The types of surface finishing methods that maintain efficacy as well as surface protection include 1) controlling the anodization layer thickness and surface area of aluminum and 2) adding a coating to fill and seal the porous anodized aluminum to provide a diffusion barrier to prevent or minimize the diffusion of the sterilizing gas or vapor through the coating. Example of such coating includes Parylene applied by vacuum deposition. The coatings may also be applied to raw aluminum.

EXAMPLES

The examples below are not limiting and are merely representative of various aspects and features of the present invention. The examples show the efficacy of coating the aluminum surface of various containers with respect to sterilization.

Example 1

Effect of Container Material

Efficacy tests were conducted with a STERRAD® 100 sterilizer (manufactured and trademarked by Advanced Sterilizations Products, Inc., a Johnson & Johnson Company) on several commercial stainless steel, anodized aluminum and raw aluminum container systems of various sizes up to approximately 20 ft$^2$ (3000 sq. in. or 2 m$^2$) of total surface area, equivalent to about two large sterilization containers. All the efficacy testing was conducted by using a biological indicator (BI) of at least 1×10$^6$ *Bacillus stearothermophilus* spores inoculated onto stainless steel coupons and placed in 3 mm by 400 mm stainless steel lumens. After processing in a STERRAD® half cycle, the BI was recovered and sterility tested at 55° C. for 14 days. Test one (Table 1) has one anodized container and one stainless steel container, test two has one anodized aluminum container and one raw aluminum container, and test three has two anodized aluminum containers. The total surface areas of containers for all three tests were about the same. The results showed that efficacy was not achieved with the test having two anodized aluminum containers in the chamber. This clearly indicates the efficacy is affected by the surface area of anodized aluminum.

TABLE 1

Effect of Anodized Aluminum Container on Efficacy of STERRAD ® 100 System (173 L chamber volume)

| Load Configuration | Surface Area of Containers (sq. in.) | | Volume of anodized coating (aluminum) oxide) | H$_2$O$_2$ (injected) | Ratio* | Efficacy |
| --- | --- | --- | --- | --- | --- | --- |
| | Total surface | Anodized surface | | | | |
| Top: Anodized Aluminum Bottom: Stainless Steel | 2673 | 1099 | 0.990 in$^3$ or 16.219 cm$^3$ | 6 mg/L or 1038 mg | 64 | Pass |
| Top: Anodized Aluminum Bottom: Raw Aluminum | 2588 | 1209 | 1.088 in$^3$ or 17.835 cm$^3$ | 6 mg/L or 1038 mg | 58 | Pass |
| Top: Anodized Aluminum Bottom: Anodized Aluminum | 2608 | 2608 | 2.346 in$^3$ or 38.444 cm$^3$ | 6 mg/L or 1038 mg | 27 | Fail |

*Ratio of H$_2$O$_2$ injected into chamber to aluminum oxide volume (mg/cm$^3$)

Example 2

Controlled Thickness of Anodized Aluminum Coatings

More work involving sterilization efficacy testing of anodized aluminum containers showed that differences in the total amount of oxide volume of an anodized aluminum surface may play a role in determining sterilization efficacy. This may be related to the amount of hydrogen peroxide absorbed by the porous oxide layer.

Several different commercially available anodized aluminum containers were evaluated to determine whether there were any physical differences among them that could account for differences in sterilization efficacy. The total coating volumes of the containers was measured to explain the different results. An electromagnetic eddy-current probe (CMI model CM223) was used to measure coating thickness. In previous testing it was showed that increasing the thickness of the anodization layer for a given amount of overall aluminum plate surface area could reduce sterilization efficacy.

It appears that the combination of thickness of the porous oxide layer and the amount of surface area together determine the sterilization efficacy. If the coating is too thick or the amount of surface area too large, sterilization efficacy is reduced. The product of average thickness and surface area can be expressed as total volume of aluminum oxide, $V = A \times t$, where t is the average oxide layer thickness and A is the total surface area. Due to variations in the different anodization processes used by different manufacturers, as well as differences in container design geometry and venting, efficacy results may be expected to vary slightly for different manufacturers.

Tables 2 and 3 show results obtained for a range of anodized aluminum containers and sheet materials, showing efficacy results, total container surface area, anodic coating thickness, and estimated oxide volume. The results show that the ratio of oxide volume on the surface to the total amount of hydrogen peroxide in the chamber (given by the product of the hydrogen peroxide vapor concentration and the chamber volume) gives a good correlation with sterilization efficacy.

TABLE 2

Efficacy tests with various Anodized Aluminum Containers with STERRAD ® 100 System (173 L chamber volume)

| Type | Surface (sq. in.) | Coating thickness (inch) | Volume of anodized coating (aluminum oxide) | $H_2O_2$ (injected) | Ratio* | Efficacy |
|---|---|---|---|---|---|---|
| Mfr. B** | 766 | .00035 | 0.268 in³ or 4.392 cm³ | 6 mg/L or 1038 mg | 236 | Pass |
| Mfr. B | 1042 | .00035 | 0.365 in³ or 5.981 cm³ | 6 mg/L or 1038 mg | 174 | Pass |
| Mfr. B | 1042 | .00042 | 0.438 in³ or 7.178 cm³ | 6 mg/L or 1038 mg | 145 | Pass |
| Mfr. B | 1042 | .00054 | 0.563 in³ or 9.226 cm³ | 6 mg/L or 1038 mg | 113 | Pass |
| Mfr. A | 706 | .000875 | 0.618 in³ or 10.127 cm³ | 6 mg/L or 1038 mg | 102 | Pass |
| Mfr. C | 1886 | .000285 | 0.538 in³ or 8.816 cm³ | 4.7 mg/L or 813.1 mg | 92 | Pass |
| Mfr. C | 2500 | .000285 | 0.713 in³ or 11.684 cm³ | 6 mg/L or 1038 mg | 89 | Pass |
| Mfr. C | 1886 | .000285 | 0.538 in³ or 8.816 cm³ | 3.5 mg/L or 605.5 mg | 69 | Pass |
| Mfr. C | 1886 | .000285 | 0.538 in³ or 8.816 cm³ | 2.4 mg/L or 415.2 mg | 47 | Fail |
| Mfr. A | 3000 | .000875 | 2.625 in³ or 43.016 cm³ | 6 mg/L or 1038 mg | 24 | Fail |
| Mfr. C | 1886 | .000285 | 0.538 in³ or 8.816 cm³ | 1.2 mg/L or 207.6 mg | 24 | Fail |

*Ratio of $H_2O_2$ injected into chamber to aluminum oxide volume (mg/cm³)
**Each letter designates a manufacturer that provided the aluminum surface to be coated.

TABLE 3

Efficacy tests with various Anodized Aluminum Sheets with STERRAD ® 100 System (173 L chamber volume)

| Type | Surface (sq. in.) | Coating thickness (inch) | Volume of anodized coating (aluminum oxide) | $H_2O_2$ (injected) | Ratio* | Efficacy |
|---|---|---|---|---|---|---|
| 5 raw Aluminum plates | 2925 | 0 | 0 in³ or 0 cm³ | 6 mg/L or 1038 mg | ∞ | Pass |
| 1 clear anodized aluminum plate, .08 mm | 585 | .00008 | 0.0468 in³ or 0.767 cm³ | 6 mg/L or 1038 mg | 1353 | Pass |

TABLE 3-continued

Efficacy tests with various Anodized Aluminum Sheets with STERRAD® 100 System (173 L chamber volume)

| Type | Surface (sq. in.) | Coating thickness (inch) | Volume of anodized coating (aluminum oxide) | $H_2O_2$ (injected) | Ratio* | Efficacy |
|---|---|---|---|---|---|---|
| 1 clear anodized aluminum plate, .09 mm | 585 | .00009 | 0.05265 in$^3$ or 0.863 cm$^3$ | 6 mg/L or 1038 mg | 1203 | Pass |
| 1 clear anodized aluminum plate, 1.85 mil | 585 | .00185 | 1.0823 in$^3$ or 17.735 cm$^3$ | 6 mg/L or 1038 mg | 59 | Pass |
| 5 clear anodized aluminum plates | 2925 | .0009 | 2.6325 in$^3$ or 43.139 cm$^3$ | 6 mg/L or 1038 mg | 24 | Fail |

*Ratio of $H_2O_2$ injected into chamber to aluminum oxide volume (mg/cm$^3$)

The testing also included variable amounts of hydrogen peroxide in the chamber (dose-response study). The data in Table 2 show that for 3 mm×400 mm stainless steel lumens inside containers and for values below about 47 mg of hydrogen peroxide per cubic centimeter of oxide coating (mg/cm$^3$) some positive BI growth was found after processing. For lumens not in containers and for values above 24 mg/cm$^3$ (Table 3) no positive BI growth was found after processing. In general, to achieve good efficacy results, one can increase the available peroxide in the sterilizer or reduce the aluminum oxide volume in the sterilizer. The volume of the aluminum oxide can be controlled or adjusted with the total anodized aluminum surface area and/or the thickness of the oxide layer.

Example 3

Parylene Coatings

The sealing process for anodized aluminum typically involves hydrating the outer layer of the oxide coating. This tends to expand the outer layer and reduces the size of pore openings. The end result is to prevent penetration of liquid into the aluminum oxide pores that may result in staining and corrosion. However, it does not effectively prevent penetration of gas or vapor into the pores. The idea of Parylene coating is to form a barrier to penetration by $H_2O_2$ and other vapors and prevent absorption of $H_2O_2$ in the anodized layer. To confirm the negative effect of anodized coating thickness and porosity on sterilization efficacy, five sheets of anodized aluminum were coated with Parylene (0.025 mm thick, Parylene coating from Specialty Coating Systems, Inc. on both sides of five aluminum sheets of anodized aluminum –0.09×12×24 inches of an approximate surface area of 20 ft$^2$). After the aluminum sheets were coated, they were subjected to 100 cycles of steam autoclave and 100 cycles of STERRAD® Process to simulate usage in a hospital environment. The coated anodized aluminum sheets were then re-tested for efficacy and demonstrated a 6-log reduction at half cycle in the STERRAD® 100 System. Results of the test are tabulated in Table 4.

TABLE 4

Efficacy tests with Anodized Aluminum Sheets coated with different coatings with STERRAD® 100 System (173 L chamber volume)

| Type | Surface (sq. in.) | Coating thickness (in.) | Volume of anodized coating (aluminum oxide) | $H_2O_2$ (injected) | Ratio* | Efficacy |
|---|---|---|---|---|---|---|
| 5 anodized aluminum plates | 2925 | 0.0009 | 2.6325 in$^3$ or 43.139 cm$^3$ | 6 mg/L or 1038 mg | 24 | Fail |
| 5 anodized aluminum plates coated with Parylene | Anodized coating covered by Parylene | Anodized coating covered by Parylene | Anodized coating covered by Parylene | 6 mg/L or 1038 mg | ∞ | Pass |

*Ratio of $H_2O_2$ injected into chamber to aluminum oxide volume (mg/cm$^3$)

Thus, these specific types of coating processes can allow the improvement and use of standard types of commercial sterilization container systems to provide good sterilization efficacy at half cycle with new sterilization processes such as low temperature hydrogen peroxide gas plasma.

It will be understood by those of skill in the art that numerous and various modifications can be made without departing from the spirit of the present invention. Therefore, it should be clearly understood that the forms of the present invention are illustrative only and are not intended to limit the scope of the present invention.

Thus, those of skill in the art will appreciate that the methods and devices described herein provide surface treated aluminum and aluminum alloys that exhibit improved sterilization process compatibility.

One skilled in the art will appreciate that these methods and devices are and may be adapted to carry out the objects and obtain the ends and advantages mentioned, as well as those inherent therein. The methods and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure.

It will be apparent to one skilled in the art that varying substitutions and modifications may be made to the invention disclosed herein without departing from the scope and spirit of the invention.

Those skilled in the art recognize that the aspects and embodiments of the invention set forth herein may be practiced separate from each other or in conjunction with each other. Therefore, combinations of separate embodiments are within the scope of the invention as disclosed herein.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the disclosure.

What is claimed is:

1. A method of sterilizing a device in a sterilizer, comprising:
    placing said device into said sterilizer, wherein said sterilizer contains a sterilization load and said sterilization load comprises an enclosure, said enclosure comprises at least one aluminum surface and said at least one aluminum surface comprises a volume of aluminum oxide;
    introducing an amount of hydrogen peroxide gas or vapor into said sterilizer, wherein the ratio of said amount of hydrogen peroxide gas or vapor introduced into said sterilizer to said volume of aluminum oxide is at least 24 $mg/cm^3$; and
    sterilizing said device in said sterilizer.

2. The method of claim 1, wherein said aluminum is anodized aluminum.

3. The method of claim 1, wherein said aluminum is raw aluminum.

4. The method of claim 1, wherein said at least one aluminum surface is coated with a material.

5. The method of claim 4, wherein said material is a polymer.

6. The method of claim 4, wherein said material is permeable to hydrogen peroxide gas or vapor.

7. The method of claim 1, wherein said enclosure is a container comprising said device, and said container comprises at least one barrier, and said ratio of said amount of hydrogen peroxide gas or vapor introduced into said sterilizer to said volume of aluminum oxide is at least 47 $mg/cm^3$;
    wherein said at least one barrier is permeable to gas or vapor and impermeable to microorganisms.

8. The method of claim 1, wherein said enclosure is a tray.

9. An enclosure for retaining a device capable of being sterilized in a sterilization process, said sterilization process comprising hydrogen peroxide, said enclosure comprising:
    a plurality of walls and a bottom surface defining an interior space, said interior space capable of retaining said device;
    at least one aluminum surface exposed to said interior, said at least one aluminum surface comprising a volume of aluminum oxide; and
    a material coated on said at least one aluminum surface, wherein said material is substantially impermeable to hydrogen peroxide gas or vapor.

10. The enclosure of claim 9, wherein said aluminum is anodized aluminum.

11. The enclosure of claim 9, wherein said aluminum is raw aluminum.

12. The enclosure of claim 9, wherein said material is a polymer.

13. The enclosure of claim 9, wherein said polymer is a polyaromatic polymer.

14. The enclosure of claim 9, wherein said polymer is parylene.

15. The enclosure of claim 9, wherein said enclosure is a tray.

16. The enclosure of claim 9, wherein said enclosure is a container.

17. A method of sterilizing a device in an enclosure, comprising:
    placing said device in said enclosure, wherein said enclosure comprises at least one aluminum surface, wherein said at least one aluminum surface comprises a volume of aluminum oxide and a material coated on said aluminum oxide; said material being substantially impermeable to hydrogen peroxide gas or vapor;
    placing said enclosure into said sterilizer;
    introducing an amount of hydrogen peroxide gas or vapor into said sterilizer; and
    sterilizing said device in said sterilizer.

18. The method of claim 17, wherein said aluminum is anodized aluminum.

19. The method of claim 17, wherein said aluminum is raw aluminum.

20. The method of claim 17, wherein said material is a polymer.

21. The method of claim 20, wherein said polymer is a polyaromatic polymer.

22. The method of claim 20, wherein said polymer is parylene.

23. The enclosure of claim 17, wherein said enclosure is a tray.

24. The enclosure of claim 17, wherein said enclosure is a container.

* * * * *